United States Patent [19]

Motoyuki et al.

[11] Patent Number: 6,153,808
[45] Date of Patent: Nov. 28, 2000

[54] METHOD FOR SEPARATING ALKYLNAPHTHALENE

[75] Inventors: Masahiro Motoyuki, Osaka; Koji Yamamoto, Kobe; Shingo Yoshida, Osaka; Yonezo Matsumoto, Osaka; Hisako Nakashima, Osaka; Midori Kumazawa, Osaka; Masaaki Matsuda, Osaka, all of Japan

[73] Assignee: Kabushiki Kaisha Kobe Seiko Sho, Kobe, Japan

[21] Appl. No.: 09/165,097

[22] Filed: Oct. 2, 1998

[30] Foreign Application Priority Data

Oct. 3, 1997 [JP] Japan ................................. 9-271495

[51] Int. Cl.⁷ ............................... C07C 7/11; C07C 7/12; B01D 53/14
[52] U.S. Cl. ............................... 585/821; 585/825; 95/84
[58] Field of Search ................................. 95/88, 84, 237; 585/821, 825

[56] References Cited

U.S. PATENT DOCUMENTS

| 3,559,376 | 2/1971 | Emery et al. . | |
|---|---|---|---|
| 4,619,970 | 10/1986 | Okamoto et al. | 536/56 |
| 4,619,984 | 10/1986 | Yuki et al. | 528/38 |

FOREIGN PATENT DOCUMENTS 0 792 858  9/1997  European Pat. Off. .

*Primary Examiner*—Tae Yoon
*Attorney, Agent, or Firm*—Oblon, Spivak, McClelland, Maier & Neustadt, P.C.

[57] ABSTRACT

In a method for separating at least one alkylnaphthalene from a stock mixture containing at least two alkylnaphthalenes selected from the group consisting of monoalkylnaphthalenes and dialkylnaphthalenes, a column packed with an optically active chromatographic packing is used for separation. The method can effectively separate a variety of alkylnaphthalenes from a mixture thereof.

6 Claims, 4 Drawing Sheets

TIME (min)

METHOD FOR SEPARATING ALKYLNAPHTHALENE

BACKGROUND OF THE INVENTION

1. Field of the Invention

The present invention relates to a method for separating at least one alkylnaphthalene from a stock mixture containing at least two alkylnaphthalenes, and particularly, relates to a method using an optically active chromatographic packing which is capable of recognizing differences in stereostructure between alkylnaphthalenes in the stock mixture containing monoalkylnaphthalenes and/or dialkylnaphthalenes.

2. Description of the Related Art

A useful alkylnaphthalene is 2,6-dimethylnaphthalene which is a starting material for polyethylene naphthalate having excellent heat resistance and gas barrier characteristics. Production of 2,6-dimethylnaphthalene includes separation of 2,6-dimethylnaphthalene from a feed stock primarily containing dimethylnaphthalene isomers. Various methods for separating the isomers have been proposed.

Among them, many separation methods using X- or Y-zeolite have been disclosed in, for example, U.S. Pat. Nos. 3,133,126, 3,114,782, 3,772,399, 3,840,610 and 4,014,949, and Japanese Patent Publication Nos. 7-29951, 52-945 and 49-27578. In these conventional methods, separation is performed based on a molecular sieve effect. That is, individual isomers have different adsorbabilities to micropores of several angstroms in zeolite by means of different molecular sizes which are caused by the difference in the position of the substituent or substituents. The isomers are separated using an eluent by a difference in solubility.

Thus, in the separation using zeolite, control of the micropore size of the zeolite has important significance. Such control has been performed by metallic cation substitution of zeolite having ion-exchange capacity. The micropore size and metallic cation substitution, however, often lack uniformity. Thus, constant separation of isomers has been performed with difficulty and low efficiencies.

SUMMARY OF THE INVENTION

Accordingly, it is an object of the present invention to provide a method for effectively separating an objective alkylnaphthalene from an alkylnaphthalene mixture.

In accordance with the present invention, in a method for separating at least one alkylnaphthalene from a stock mixture containing at least two alkylnaphthalenes selected from the group consisting of monoalkylnaphthalenes and dialkylnaphthalenes, the method is characterized by using a column packed with an optically active chromatographic packing for separation. The optically active chromatographic packing can effectively separate mixed alkylnaphthalenes.

Preferably, the optically active chromatographic packing comprises a support carrying at least one derivative selected from the group consisting of cellulose ester derivatives, cellulose carbamate derivatives, and ligand derivatives. The support is preferably an inorganic support having a particle size of 5 to 300 μm and pores of a diameter in a range of 20 to 1,000 angstroms. More preferably, the inorganic support is selected from the group consisting of silica gel, alumina, zeolite, and bentonite.

The stock mixture may contain a mixture of monoalkylnaphthalene isomers and/or dialkylnaphthalene isomers. Alternatively, the stock mixture may contain at least two alkylnathhalenes selected from the group consisting of 2,6-dimethylnaphthalene, 2,7-dimethylnaphthalene, 2,3-dimethylnaphthalene, 1,2-dimethylnaphthalene, 1,3-dimethylnaphthalene, 1,4-dimethylnaphthalene, 1,5-dimethylnaphthalene, 1,6-dimethylnaphthalene, 1,7-dimethylnaphthalene, 1,8-dimethylnaphthalene, 1-methylnaphthalene, and 2-methylnaphthalene. In particular, the method in accordance with the present invention is suitable for separating 2,6-dimethylnaphthalene from a stock mixture containing 2,6-dimethylnaphthalene and 2,7-dimethylnaphthalene. No conventional method can easily separate these isomers.

The present invention also involves 2,6-naphthalene dicarboxylic acid or its ester which is made by oxidation or oxidation-esterification of 2,6-dimethylnaphthalene being separated by the above-described method. The resulting 2,6-naphthalene dicarboxylic acid or its ester can be used as a part or all of monomer components for manufacturing a polymeric compound. In particular, it can be preferably used as a part or all of dicarboxylic acid components in production of polyethylene naphthalate or polybutylene naphthalate.

DESCRIPTION OF THE PREFERRED EMBODIMENT

Figure 1:
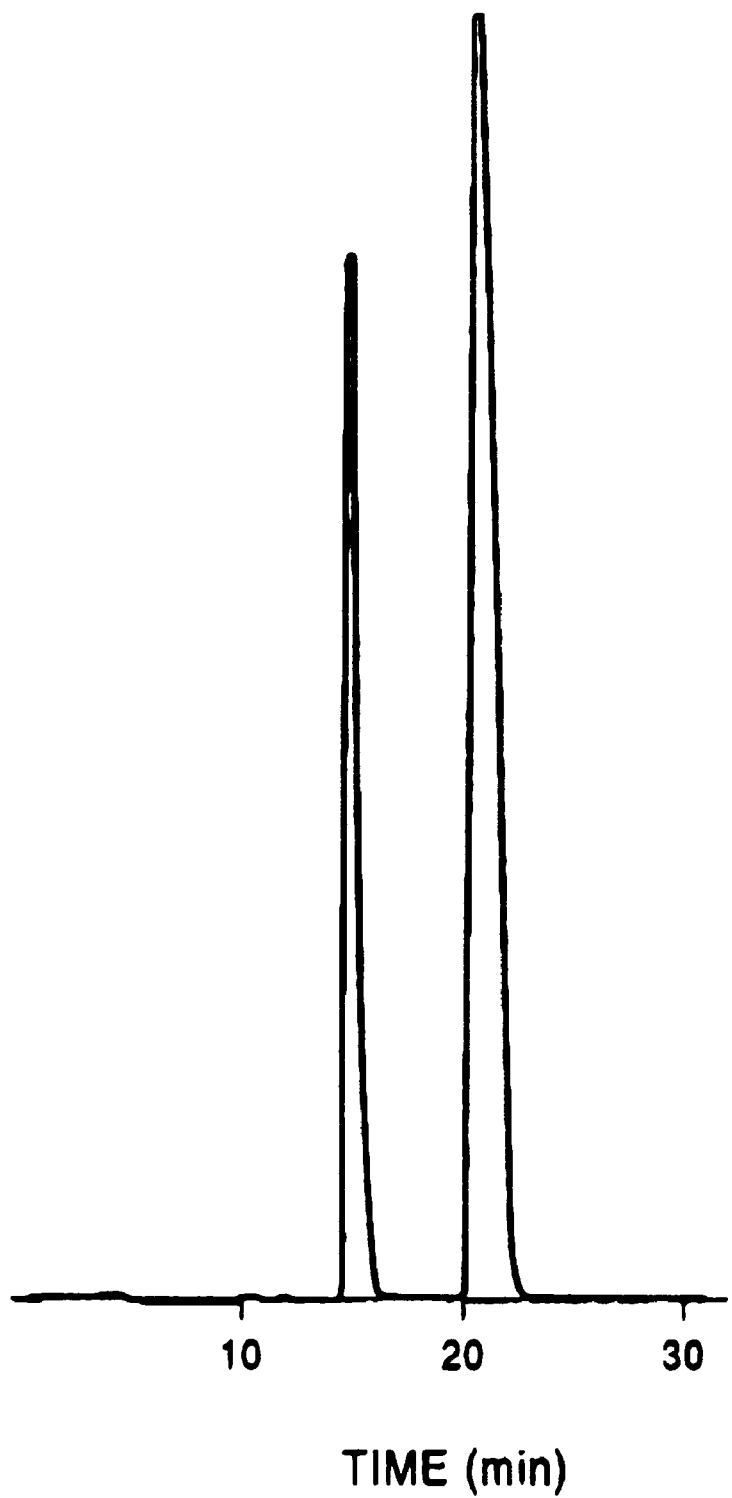
FIG. 1 is a chromatogram showing the result of Example 1.

The present inventors have intensively studied a method for separating at least one alkylnaphthalene from an alkylnaphthalene mixture, and have discovered that an optically active chromatographic packing can recognize differences in stereostructure between alkylnaphthalene isomers. The present invention, therefore, has been completed.

The stock mixture used for separation in the present invention is a mixture containing monoalkylnaphthalenes and/or dialkylnaphthalenes. Alkylnaphthalene means a derivative of naphthalene having at least one alkyl group. Thus, alkylnaphthalenes include, not only monoalkylnaphthalenes and dialkylnaphthalenes, but also tri- or higher substituted derivatives. Since tri- or higher substituted derivatives can be separated from mono- and/or di-alkylnaphthalenes by any known method other than chromatographic methods, the present invention targets the separation of mono- and/or di-alkylnaphthalenes which are separable with difficulty by methods other than chromatographic methods. Thus, the mono- and/or di-alkylnaphthalenes in the present invention include derivatives having different alkyl groups and isomers thereof.

Examples of mono- and/or di-alkylnaphthalenes include monoalkylnaphthalenes, e.g. 1-methylnaphthalene, 2-methylnaphthalene, 1-ethylnaphthalene, and 2-ethylnaphthalene; and dialkylnaphthalenes, e.g. 2,6-dimethylnaphthalene, 2,7-dimethylnaphthalene, 1,3-dimethylnaphthalene, 1,6-dimethylnaphthalene, 1,7-dimethylnaphthalene, 2,3-dimethylnaphthalene, 1,2-dimethylnaphthalene, 1,4-dimethylnaphthalene, 1,5-dimethylnaphthalene, 1,8-dimethylnaphthalene, 2,6-diethylnaphthalene, 2,7-diethylnaphthalene, 1,3- diethylnaphthalene, 1,6-diethylnaphthalene, 1,7-diethylnaphthalene, 2,3-diethylnaphthalene, 1,2-diethylnaphthalene, 1,4-diethylnaphthalene, 1,5-diethylnaphthalene, and 1,8-diethylnaphthalene.

The stock mixture may contain at least two monoalkylnaphthalenes and/or dialkylnaphthalenes, for example, a monoalkylnaphthalene and a dialkylnaphthalene, two or more monoalkylnaphthalenes and two or more dialkylnaphthalenes, at least two monoalkylnaphthalenes or dialkylnaphthalenes having different alkyl groups, isomers of a monoalkylnaphthalene or dialkylnaphthalene, a mixture of isomers of a monoalkylnaphthalene and a dialkylnaphthalene, and a mixture thereof.

The separation method in accordance with the present invention is simple and highly efficient and can be preferably applied to separation of a mixture of isomers which are separated with difficulty by any conventional method. In particular, the method is suitable for separation of 2,6-dialkylnaphthalene and 2,7-dialkylnaphthalene which have very similar boiling points and melting points.

The separation method in accordance with the present invention is performed by passing the stock mixture through a column packed with an optically active chromatographic packing. The optically active chromatographic packing is generally used for separating optical isomers. In the present invention, it has been found that the packing can separate various alkylnaphthalenes based on the difference in their structures. Thus, the use of the optically active chromatographic packing is essential for the present invention. Separation effects of the optically active chromatographic packing probably appear by hydrophobic interaction and π—π interaction between the functional group of the packing and alkylnaphthalenes. Thus, the separation effects have a quite different mechanism from the conventional molecular sieve effect.

A usable optically active chromatographic packing has different adsorbabilities to various alkylnaphthalenes. Examples of such packing materials (hereinafter referred to as separation compounds) include cellulose ester derivatives e.g. cellulose tris(4-methylbenzoate), cellulose tris(4-ethylbenzoate), and cellulose tris(5-methylbenzoate); cellulose carbamate derivatives, e.g. cellulose tris(3,5-dimethylphenylcarbamate) and cellulose tris(3,5-diethylphenylcarbamate); and ligands e.g. ruthenium trisphenanthroline. These separation compounds are used alone or in combination by adsorbing onto or reacting with a carrier.

Separation compounds which are insoluble in the stock mixture and have a desired particle size and satisfactory mechanical strength may be used alone as chromatographic packings for separation. It is preferable that these separation compounds be used after they are carried on supports by adsorption or binding in view of mechanical strength.

Examples of supports include conventional inorganic porous supports, such as silica gel, alumina, zeolite, and bentonite. Preferably, the support has micropores having a diameter of 20 to 1,000 angstroms. The diffusion rate of alkylnaphthalene into micropores having a pore size of less than 20 angstroms will decrease, hence the functional groups of tho separation compound are not effectively used during separation, resulting in a reduced separation efficiency. A support including micropores having a diameter of more than 1,000 angstroms has a small surface area, hence it can carry a reduced amount of separation compound per unit weight, resulting in a reduced separation efficiency.

The particle size of the support may be determined depending on the conditions for separating alkylnaphthalenes. In general column separation, supports having a size of 1 to 300 μm are preferably used. A column packed with a support having a size of less than 1 μm requires a high liquid pressure and inhibits the separation operation. A column packed with a support having a size of larger than 300 μm causes delayed diffusion of alkylnaphthalenes in micropores of the support, and thus causes deterioration of the separation efficiency. The support may contain a fraction of particles which lie out of the preferable range.

The separation compound may be carried onto a support by any known adsorption or chemical process. Alternatively, a commercially available optically active chromatographic packing may be used in the present invention. Examples of such packings include "CHIRALCEL OD" and "CHIRALCEL OJ" made by Daicel Chemical Industries, Ltd. and "Ceramospher Chiral RU-1" and "Ceramospher Chiral RU-2" made by Shiseido Co., Ltd.

In the separation of alkylnaphthalenes, a stock mixture is placed into a column packed with an optically active chromatographic packing to be adsorbed, and then eluted. Elution chromatography or a continuous separation process such as a pseudo-mobile bed method may be used in the separation. Although the stock mixture may be composed purely of alkylnaphthalenes, it is preferably used as a solution. Non-limiting examples of solvents for dissolving alkylnaphthalenes include aliphatic hydrocarbons, e.g. hexane and heptane; aromatic hydrocarbons, e.g. toluene, xylene, benzene, and 1-methylnaphthalene; and polar solvents, e.g. acetonitrile, methanol, and propanol. These solvents may be used alone or in combination.

Conditions for putting the optically active chromatographic packing into contact with the stock mixture are determined in consideration of the scale of the separating unit, the type of packing, types of alkylnaphthalenes in the stock mixture, and types of solvents and eluents. In general, 0.01 to 10 parts by weight of optically active chromatographic packing is put into contact with 100 parts by weight of alkylnaphthalenes. The contact time (pass time) of the stock mixture in the column is generally 5 minutes to 24 hours, and the contact temperature is generally 0° C. to 100° C.

Alkylnaphthalenes are adsorbed when the stock mixture passes through the column packed with the optically active chromatographic packing, and then separately eluted by pouring an eluent into the column. All the solvents described above can be used as eluents. It is preferred that 300 to 30,000 parts by weight of eluent be used to 100 parts by weight of optically active chromatographic packing. The preferred contact time is 5 minutes to 24 hours, and the preferred contact temperature is 10° C. to 100° C.

As described above, the present invention relates to a novel method for separating alkylnaphthalenes from a stock mixture using an optically active chromatographic packing and which has industrial significance.

According to the present invention, 2,6-dialkylnaphthalene can be readily separated from a stock mixture containing 2,6-dialkylnaphthalene and 2,7-dialkylnaphthalene which have very similar boiling points and melting points. Oxidation by any known method of 2,6-dialkylnaphthalene produces 2,6-naphthalene dicarboxylic acid. Oxidation and esterification of 2,6-dialkylnaphthalene produces ester of 2,6-naphthalene dicarboxylic acid. The carboxylic acid and ester can be used as a part or all of monomer components in production of a polymeric compound. For example, 2,6-naphthalene carboxylic acid and its ester are useful as an acid component in production of polyesters, such as polyethylene naphthalate and polybutylene naphthalate.

As described above, the method in accordance with the present invention can easily separate a variety of alkylnaphthalenes by column chromatography using an optically active chromatographic packing. In particular, 2,6-dimethylnaphthalene and 2,7-dimethylnaphthalene, which are not satisfactorily separated by conventional methods, can be effectively separated. Thus, the method in accordance with the present invention can cause the use of 2,6-dimethylnaphthalene to spread, such as being used as a monomer for a polymeric compound.

EXAMPLES

The present invention will now be described in more detail based on the following Examples, which are not for limiting the present invention. Thus, many apparently widely different embodiments of this invention may be made without departing from the spirit and scope thereof.

Example 1

A column having an inner diameter of 4.6 mm and a length of 25 cm was packed with 2.21 g of an optically active chromatographic packing to prepare an optically active separation column A. The optically active chromatographic packing was composed of cellulose tris(3,5-dimethylphenylcarbamate) carried onto silica gel having an average pore size of 100 angstroms and an average particle size of 10 μm. From the top of the column A. 0.005 ml of a hexane solution containing 0.05 mg of 2,6-dimethylnaphthalene and 0.025 mg of 2,7-dimethylnaphthalene was injected. Immediately after this, a mixture of hexane/2-propanol 1000/1 was fed into the column at a flow rate of 60 ml/hour for 30 minutes. As shown in FIG. 1, 2,7-dimethylnaphthalene and then 2,6-dimethylnaphthalene were separately eluted. The separation factor α between 2,6-dimethylnaphthalene and 2,7-dimethylnaphthalene was 1.52.

Example 2

Figure 2:
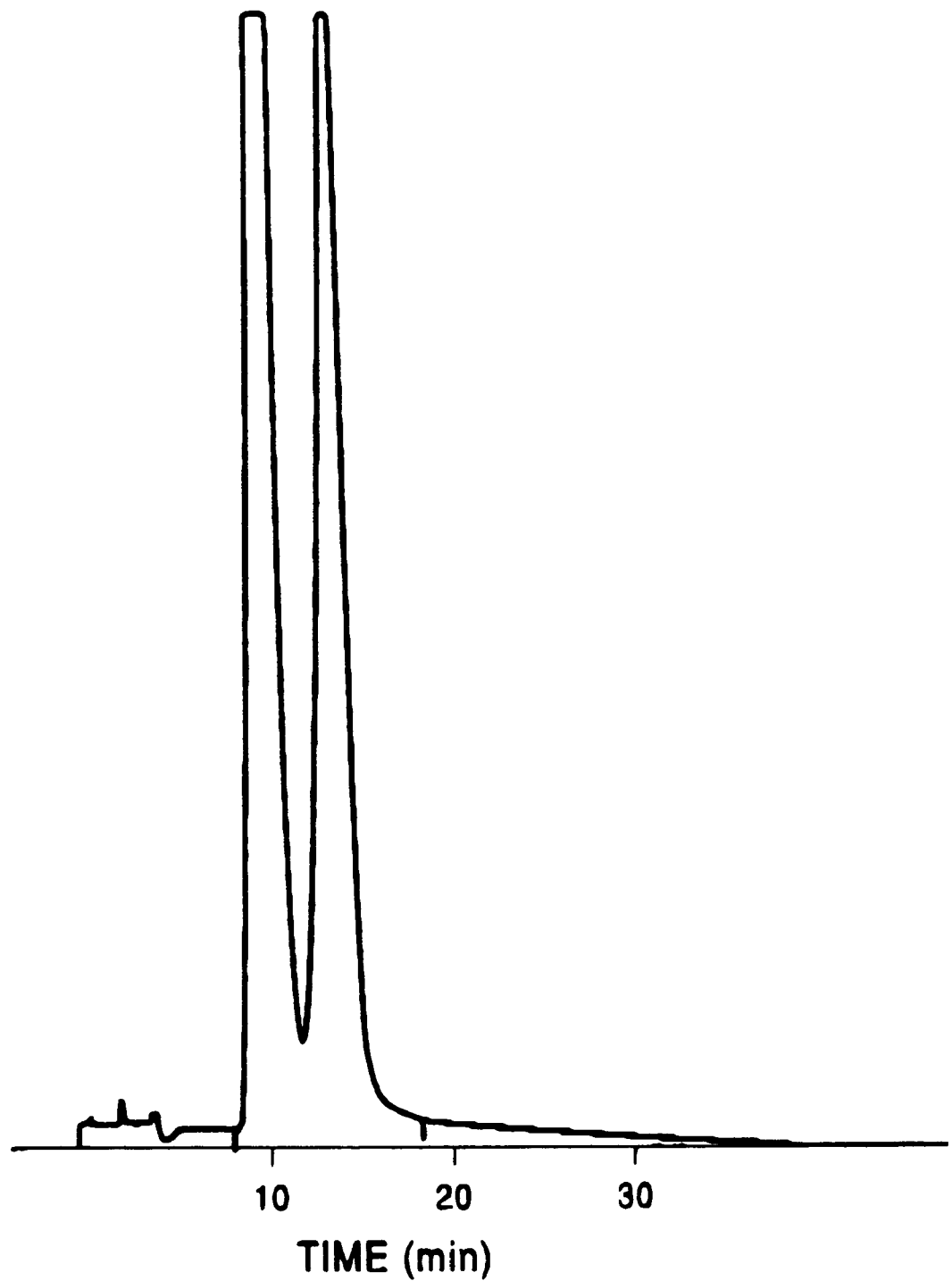
FIG. 2 in a chromatogram showing the result of Example 2.

A column having an inner diameter of 4.6 mm and a length of 25 cm was packed with 2.13 g of an optically active chromatographic packing to prepare an optically active separation column B. The optically active chromatographic packing was composed of ruthenium tris(1,10-phenanthroline) carried by ion exchange onto magnesium/sodium silicate clay having an average pore size of 40 angstroms and an average particle size of 5 μm. Separation was performed using the column B as in Example 1. As shown in FIG. 2, 2,6-dimethylnaphthalene and then 2,7-dimethylnaphthalene were separately eluted. The separation factor α between 2,6-dimethylnaphthalene and 2,7-dimethylnaphthalene was 1.52.

Example 3

Figure 3:
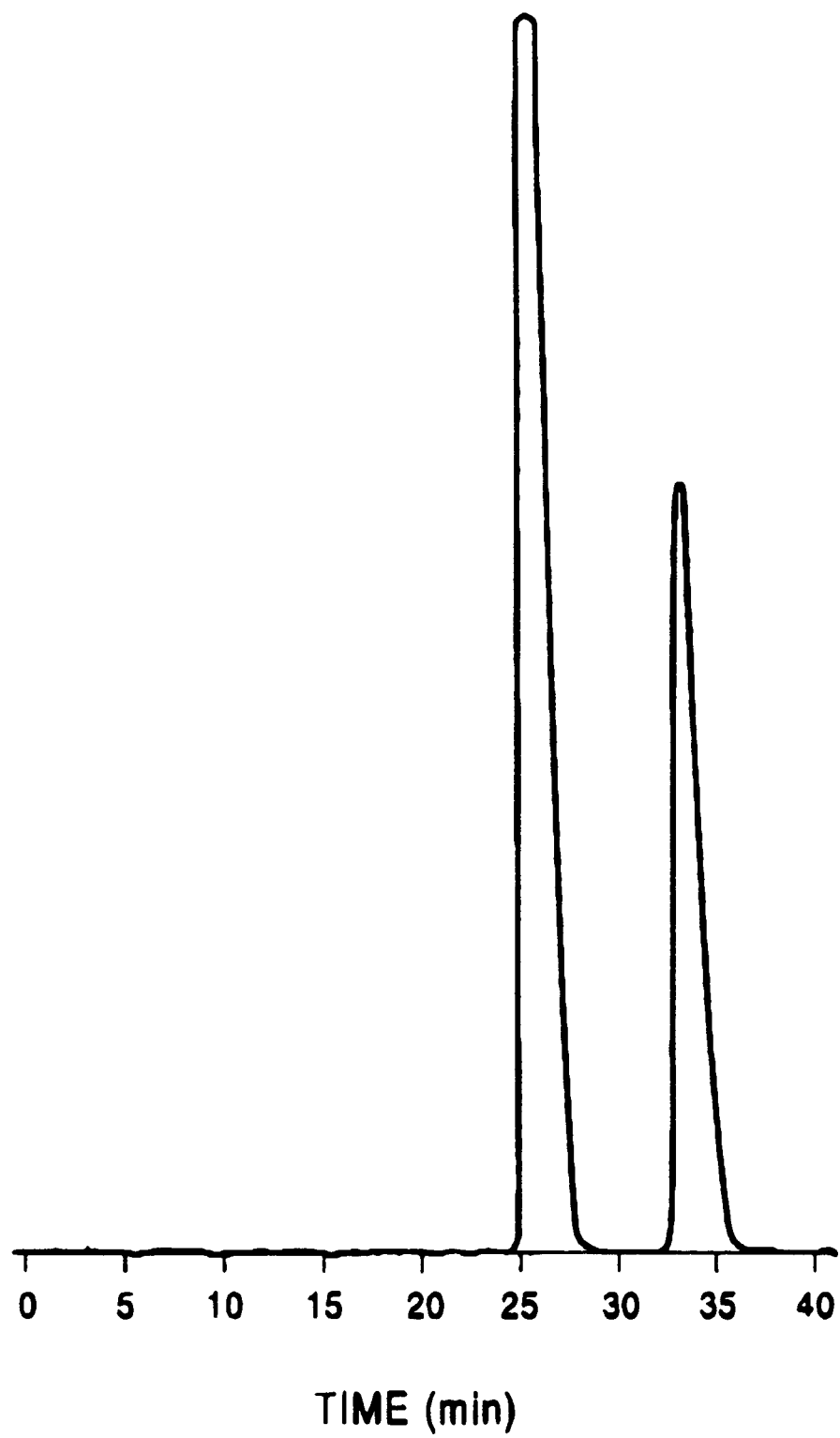
FIG. 3 is a chromatogram showing the result of Example 3.

A column having an inner diameter of 4.6 mm and a length of 25 cm was packed with 2.14 g of an optically active chromatographic packing to prepare an optically active separation column C. The optically active chromatographic packing was composed of cellulose tris(4-methylbenzoate) carried onto silica gel having an average pore size of 120 angstroms and an average particle size of 5 μm. From the top of the column C. 0.005 ml of the hexane solution in Example 1 was injected, and immediately after, a mixture of hexane/2-propanol 1000/1 was fed into the column at a flow rate of 60 ml/hour for 40 minutes. As shown in FIG. 3, 2,7-dimethylnaphthalene and then 2,6-dimethylnaphthalene were separately eluted. The separation factor α between 2,6-dimethylnaphthalene and 2,7-dimethylnaphthalene was 1.37.

Examples 4 to 7

Optically active separation columns D, E, F and G were prepared by carrying cellulose tris(4-methylbenzoate) on silica gals having an average pore size of 300 angstroms, 500 angstroms, 1,000 angstroms, and 5,000 angstroms, respectively. Separation characteristics between 2,6-dimethylnaphthalene and 2,7-dimethylnaphthalene were determined as in Example 3. The separation factor α was 1.52 for the column D, 1.32 for the column E, 1.26 for the column F, and 1.15 for the column G.

Example 8

Figure 4:
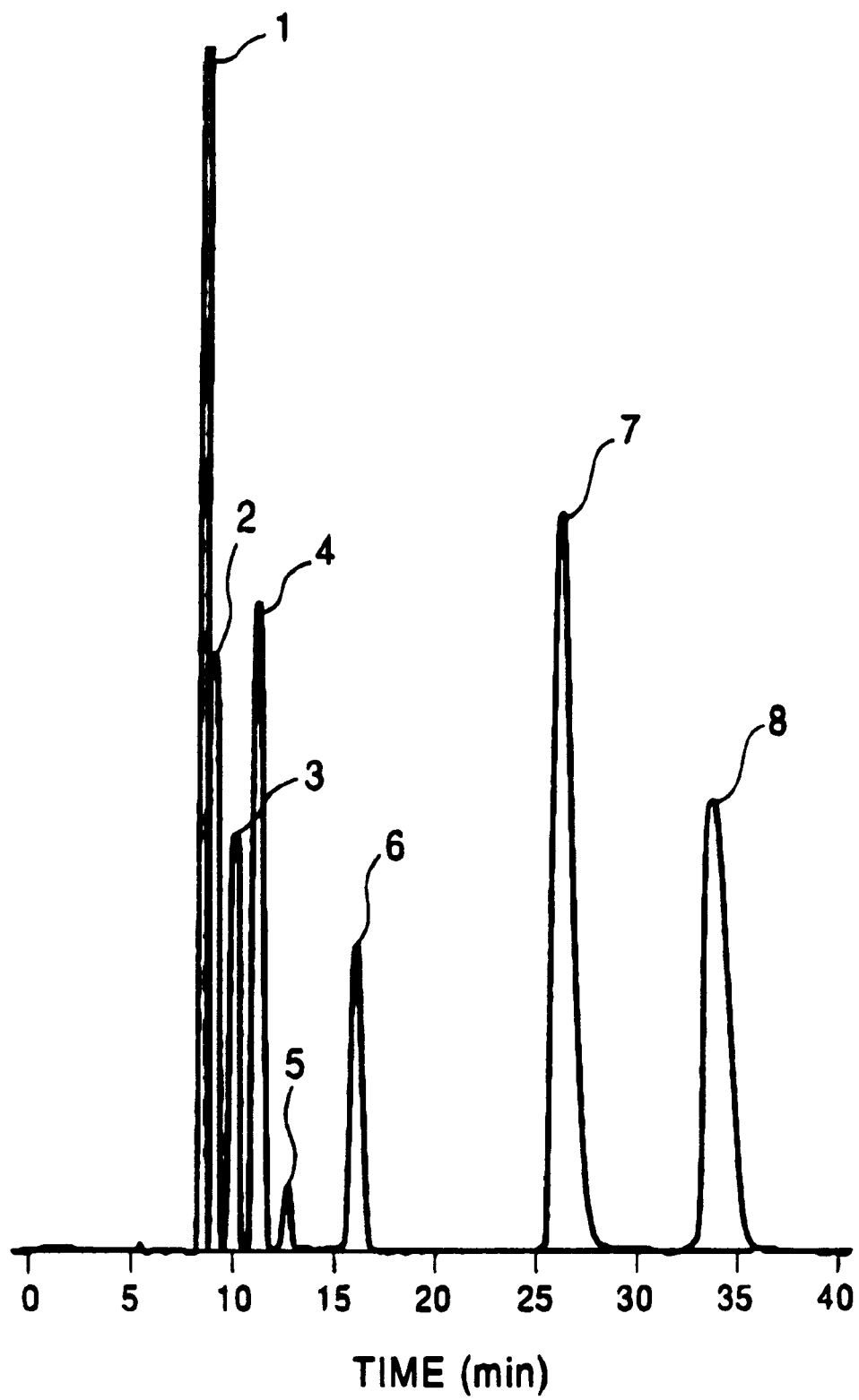
FIG. 4 is a chromatogram showing the result of Example 8.

A hexane solution was prepared. The solution contained 1 mg of a mixture having the following composition per 1 ml: 21.1% 1,7-dimethylnaphthalene (① in FIG. 4), 8.2% 1,3-dimethylnaphthalene (② in FIG. 4), 6.5% 1-methylnaphthalene (③ in FIG. 4), 11.4% 1,6-dimethylnaphthalene (④ in FIG. 4), 0.2 naphthalene (⑤ in FIG. 4), 6.0% 2-methylnaphthalene (⑥ in FIG. 4), 24.2% 2,6-dimethylnaphthalene (⑦ in FIG. 4), and 21.5% 2,7-dimethylnaphthalene (⑧ in FIG. 4). Onto the top of the separation column C prepared in Example 3, 5 μl of hexane solution was injected, and a mixture of hexane/2-propanol= 250/1 by weight was fed at a flow rate of 60 ml/hour for 40 minutes. The results of the separation are shown in FIG. 4.

What is claimed is:

1. A method for separating at least 2,6-dimethylnaphthalene from 2,7-dimethylnaphthalene contained in a stock mixture containing at least two alkylnaphthalenes comprising passing said stock mixture through a column packed with an optically active chromatographic packing material.

2. The method according to claim 1, wherein said optically active chromatographic packing support comprises at least one derivative selected from the group consisting of cellulose tris(4-methylbenzoate), cellulose tris(4-ethylbenzoate), cellulose tris(5-methylbenzoate), cellulose tris(3,5-dimethylphenylcarbamate), cellulose tris(3,5-diethylphenylcarbamate), ruthenium trisphenanthroline and mixtures thereof.

3. The method according to claim 2, wherein said support is an inorganic support having a particle size of 5 to 300 μm and pores of a diameter in a range of 20 to 1,000 angstroms.

4. The method according to claim 3, wherein said inorganic support is selected from the group consisting of silica gel, alumina, zeolite, and bentonite.

5. The method according to claim 1, wherein said stock mixture contains a mixture of monoalkylnaphthalene isomers and dialkylnaphthalene isomers.

6. The method according to claim 1, wherein said stock mixture comprises 2,6-dimethylnaphthalene, 2,7-dimethylnaphthalene and one or more alkylnaphthalene selected from the group consisting of 2,3-dimethylnaphthalene, 1,2-dimethylnaphthalene, 1,3-dimethylnaphthalene, 1,4-dimethylnaphthalene, 1,5-dimethylnaphthalene, 1,6-dimethylnaphthalene, 1,7-dimethylnaphthalene, 1,8-dimethylnaphthalene, 1-methylnaphthalene, and 2-methylnaphthalene.

* * * * *